United States Patent

Brown

[11] 4,162,313
[45] Jul. 24, 1979

[54] PHENOXYBENZYLPHOSPHONIUM SALT INSECTICIDES

[75] Inventor: Michael J. Brown, Randolph Township, Morris County, N.J.

[73] Assignee: GAF Corporation, New York, N.Y.

[21] Appl. No.: 861,204

[22] Filed: Dec. 16, 1977

[51] Int. Cl.$^2$ ............................................. A01N 9/36
[52] U.S. Cl. ............................. 424/217; 260/570.5 R; 260/606.5 F; 424/211; 424/214
[58] Field of Search .................. 424/217; 260/606.5 F

[56] References Cited

U.S. PATENT DOCUMENTS 3,804,950  4/1974  Diamond .............................. 424/198

Primary Examiner—Allen J. Robinson
Attorney, Agent, or Firm—Walter C. Kehm; Marilyn J. Maue

[57] ABSTRACT

The insecticides having the formula:

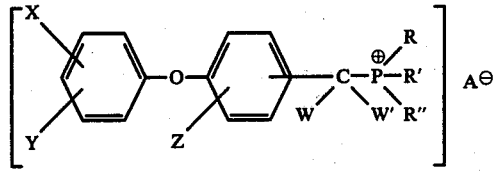

wherein $A^\ominus$ is a halogen anion; X, Y and Z are each independently hydrogen, a halogen atom or haloalkyl group of from 1 to 4 carbon atoms; R, R' and R" are each independently phenyl, halophenyl, haloalkylphenyl of from 7 to 12 carbon atoms or alkyl of from 1 to 6 carbon atoms, optionally substituted with halogen; W is hydrogen, —CHO or —CHN(R''')$_2$ where each R''' is independently hydrogen or alkyl of from 1 to 4 carbon atoms, optionally substituted with halogen; and W' is hydrogen or represents a bond forming a double bond between C and W when W is —CHN(R''')$_2$. The invention also relates to the method of preparing formulations or compositions of said insecticides together with their use as agricultural products.

15 Claims, No Drawings

PHENOXYBENZYLPHOSPHONIUM SALT INSECTICIDES

This application relates to a new class of insecticidal compounds, a process for their preparation and the application of said compounds utilized either alone as an agricultural chemical or in chemical formulations with a carrier.

The compounds of this invention find utility as pesticides having particular efficacy as insecticides which are ecologically safe and leave no toxic residue in the plants.

For the purpose of the present disclosure, the term pesticide is intended to describe insecticides.

It is an object of this invention to provide new and useful pesticides which are not harmful to the environment.

Still another object is to provide novel insecticides for coleopterous insects and other pests.

Another object of the present invention is to provide insecticides having a high selectivity for beetles, while having substantially no detrimental effect on crops.

Yet another object of this invention is to provide formulations for the present pesticides for applications as sprays or dusts.

These and other objects of the present invention will become apparent from the following description and disclosure.

According to this invention, there is provided phosphonium salt pesticide having the formula:

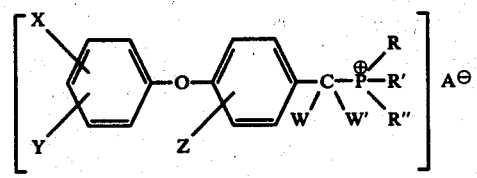

wherein $A^\ominus$ is a halogen anion; X, Y and Z are each independently hydrogen, a halogen atom or a haloalkyl group of from 1 to 4 carbon atoms; R, R' and R" are each independently phenyl, halophenyl, haloalkyphenyl of from 7 to 12 carbon atoms or alkyl of from 1 to 6 carbon atoms, optionally substituted with halogen; W is hydrogen, —CHO or —CHN(R''')$_2$ where each R''' is independently hydrogen or alkyl of from 1 to 4 carbon atoms, optionally substituted with halogen; and W' is hydrogen or represents a bond forming a double bond between C and W when W is —CHN(R''')$_2$. The halogen referred to in the above phosphonium salt compounds is fluorine, chlorine, bromine or iodine.

Of the above group of compounds, those wherein one of X or Y is hydrogen and the other is halogen or perhaloalkyl, W and W' and hydrogen, R, R' and R" are the same and are either lower alkyl or phenyl and $A^\ominus$ is a bromine or chlorine anion are preferred as pesticides in the present invention.

Most preferred as insecticides of the present invention are those having the formula:

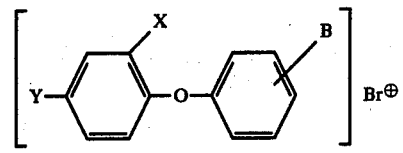

wherein X is hydrogen or chlorine; Y is hydrogen or trifluoromethyl, and where one of X and Y is other than hydrogen; and B is —CH$_2$P$^+$(R)$_3$ where R is butyl or phenyl.

In general, the phenoxy benzyl phosphonium compounds of the present invention may be prepared according to the reaction illustrated by the following equation I, wherein the reactants in each stage are contacted in a mole ratio of between about 1:2 and about 2:1, preferably stochiometric amounts of the required reactants, and the various reactions are effected at a temperature between about 0° C. and about 180° C. under from about 5 to about 25 psig pressure, more desirably between about 5° C. and about 150° C. under atmospheric pressure. Stage (2) of the reaction is beneficially carried out in the presence of a peroxy type catalyst, e.g. benzoyl peroxide. Under most preferred conditions, reaction (3) is carried out at between about 10° C. and 35° C. under atmospheric pressure. The reaction, usually carried out over a period of from about 30 minutes to about 4 hours, is effected in liquid phase with an organic solvent; chloroform being illustrative of the solvents selected for stage (3) of the reaction with a phosphine. It is to be understood, however, that other solvents, such as xylene, toluene, bromoform, methyl isobutyl ketone, dichloromethane, carbontetrachloride, ethanol, propanol, dimethylformamide, 2-methoxyethyl ether, or other solvents conventionally employed for quaterinization reactions, may be substituted, in the whole or in part, for chloroform in stage (3) of the reaction illustrated by Equation I.

Since the product of stage (1) between a halogenated benzene and the metal oxide of a toluene and the product of stage (2) between a halogenated phenyl benzyl ether and N-bromosuccinimide are known, the novel stage in process of the present invention may be considered to reside in stage (3) where phenoxybenzylbromide or other halide such as the corresponding chloride or iodide, is reacted with a trisubstituted phosphine to provide the novel quaternized product.

Since the phenoxybenzyl halide reactants of stage (3) in Equation I are generally known in the art, alternative methods for the preparation of the correspondingly substituted phenoxy benzylphosphonium quaternized salts will become apparent to those skilled in the art from this disclosure. For example, free radical halogenation of the phenoxybenzyl product of stage (1) in the absence or presence of a catalyst such as a metal halide or UV light can be effected to produce the corresponding halomethyl analogue or reactant of stage (3).

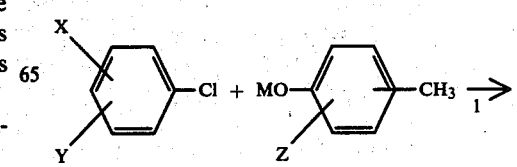

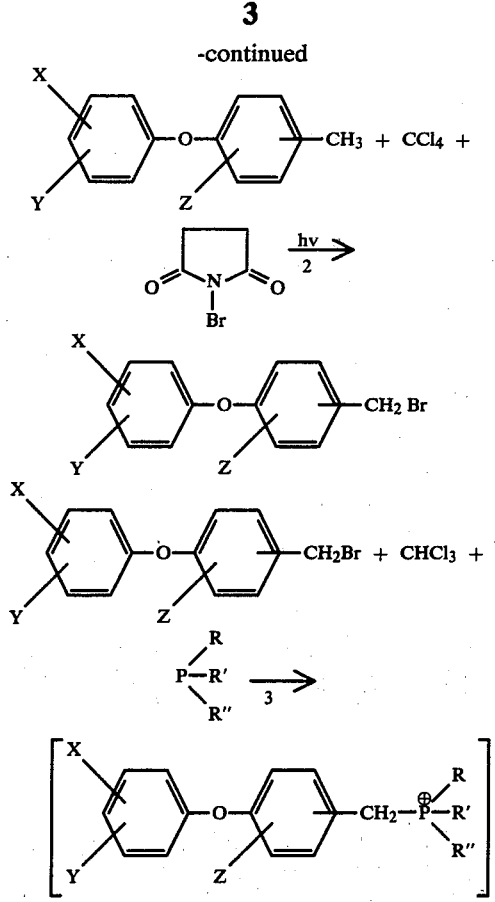

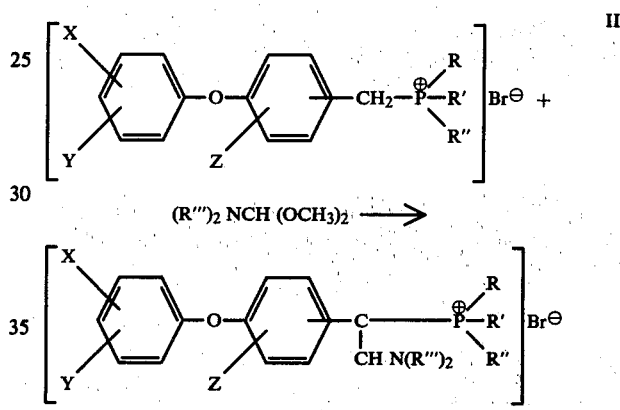

In the above reaction, M represents an alkali metal, such as Li, Na, K or Ca; Na or K being preferred, X, Y, Z, R, R' and R" have the meaning set forth above for Formula I. The product of stage 3 can be isolated and recovered by distilling off solvent and then triturating the product with petroleum ether, cyclohexane or other inert triturating agent. The corresponding chliride anion may be obtained from the final product of Equation I by a substitution reaction in which the bromine of the product reacts with an excess of sodium- or potassium- chloride in aqueous solution. The substitution reaction is effected under atmospheric pressure at a temperature of between about 5° C. and about 150° C. in the presence of chloroform or any other suitable water-immiscible inert solvent.

The corresponding fluoride or iodide anions may be obtained from the product of Equation I by phase-transfer. Generally, to obtain the various halide anions of the present invention, the product of reaction (3) in Equation I is dissolved in chloroform or other suitable solvent, such as bromoform or any water-immiscible inert solvent. To this solution an aqueous alkali metal halide or ammonium halide solution, wherein the halide of the alkali metal or ammonium salt is capable of replacing the bromine anion of the phosphonium compound, is added with agitation until two liquid layers are formed; usually within a period of from 15 minutes to 4 hours. The preferred alkali metal halides are the iodide or fluoride of sodium or potassium.

The phase-transfer reaction is carried out at a temperature between about 5° C. and about 125° C. preferably between about 10° C. and about 100° C., under atmospheric conditions. The substituted halide anion product is recovered by drawing off the lower liquid product phase or by decanting the upper liquid aqueous alkali metal halide or ammonium halide phase. The product is then isolated by evaporating the lower product phase to dryness, washing the product with water, followed by evaporation to dryness. The washing and drying operation can be repeated as desired.

To obtain the amino substituted phosphonium salt of the present invention, the final product of Equation I, or the corresponding chloride, fluoride, or iodide anion of the product of Equation I, is reacted with an aminodimethoxymethane in an anhydrous alcoholic solution, e.g. an anhydrous solution of ethanol, propanol, butanol, pentanol, or another inert organic solvent. This reaction is carried out at a temperature of between about 10° C. and about 180° C. under from about 5 psig to about 30 psig, preferably at a temperature between about 80° C. and about 140° C. under atmospheric pressure. The following Equation II exemplifies such a viabile process for the preparation of the amino substituted phosphonium compounds of the present invention using bromine anion for purposes of illustration.

In the above equations, X, Y, Z, R, R', R" and R'" have the meaning set forth in Formula I of the preceeding disclosure.

The above amino substituted product is recovered from the reaction mixture by evaporation to dryness to remove alcoholic by-product and trituration with petroleum ether, cyclohexane or any other inert agent conventionally employed for forming a fine particulate solid or powder.

To obtain the aldehyde derivative of the phosphonium salt of the present invention, the product of Equation II, or the corresponding fluoride, chloride or iodide anion of said product, is reacted with an aqueous solution of mineral acid such as a 2 to 50% solution of HCl, $H_2SO_4$, $HNO_3$, etc., at a temperature of between about 25° C. and about 100° C. under from about 5 psig to about 30 psig; preferably between about 50° C. and about 80° C. under atmospheric pressure. The corresponding aldehyde substituted phosphonium compound is formed within a period of from about 15 minutes to about 1.5 hours and is recovered from the reaction mixture by extraction with chloroform or another inert organic solvent conventionally employed for removing acid impurities. The solvent is then evaporated and the product triturated with a suitable agent, such as petroleum ether.

The following Equation III illustrates such a viable process for the preparation of the aldehyde derivative of the halogenated phenoxybenzyl phosphonium compound.

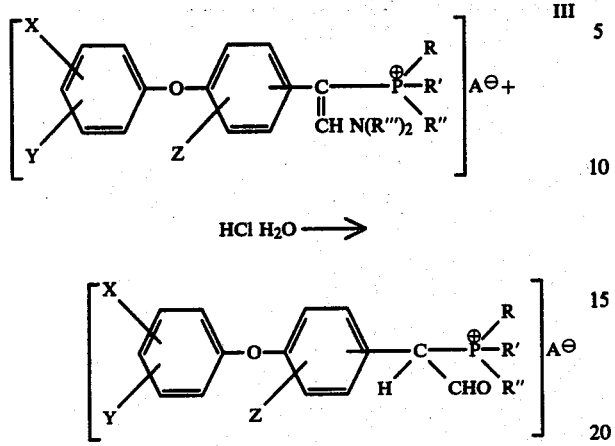

The product of Equation III may be converted into the corresponding dehydrohalogenated compound as shown in Equation IV. The conversion is effected by passing the aldehyde substituted phosphonium compound (e.g. the product of Equation III) downwardly through an anion exchange column (e.g. Amberlite CG-4B, 200-400 mesh) in an alcohol solution, e.g. a methanol solution, at ambient temperature. The product is then isolated by evaporation to dryness followed by trituration with cylohexane or petroleum ether or any other conventional trituration liquid. As indicated, the product of Equation IV exists in equilibrium.

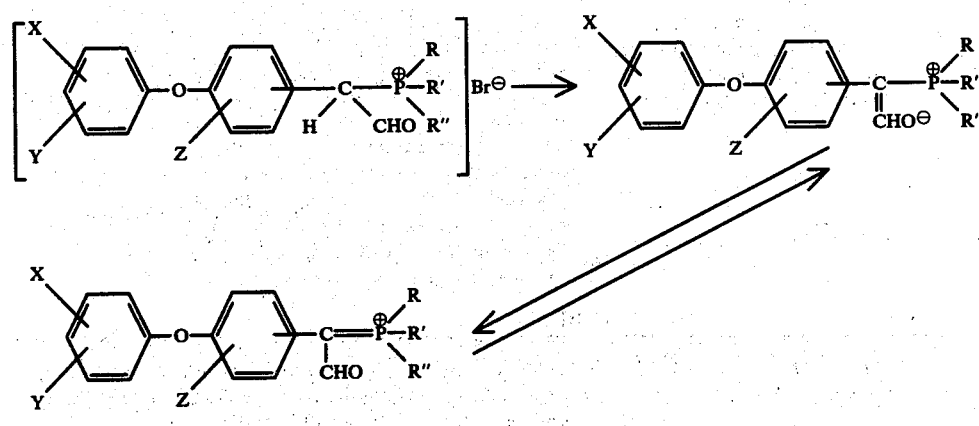

The following compounds shown in Table I are representative of the novel compounds of the present invention.

TABLE I

| Compound Number | Structure | °C. Melt Pt. |
|---|---|---|
| 1 | [structure with Cl, O, CH₂P⁺(C₄H₉)₃, Br⁻] | 145-7 |
| 2 | [structure with Cl, O, CH₂P⁺(C₄H₉)₃, Br⁻] | 115-9 |
| 3 | [structure with CF₃, Cl, O, CH₂P⁺(C₄H₉)₃, Br⁻] | 88-90 |
| 4 | [structure with CF₃, Cl, O, CH₂P⁺(C₂H₅)₃, Br⁻] | 144-6 |
| 5 | [structure with Cl, O, CH₂P⁺(C₂H₅)₃, Br⁻] | 144-6 |
| 6 | [structure with Cl, O, CH₂P⁺(C₂H₅)₃, Br⁻] | 119-21 |
| 7 | [structure with Cl, O, CH₂P⁺(C₂H₅)₃, Br⁻] | 151-3 |
| 8 | [structure with Cl, O, CH₂P⁺(C₄H₉)₃, Br⁻] | 88-90 |
| 9 | [structure with Cl, O, CH₂-P⁺(C₆H₅)₃, Br⁻] | 243-50 |
| 10 | [structure with Cl, O, CH₂P⁺(C₆H₅)₃, Br⁻] | 105 |
| 11 | [structure with CF₃, Cl, O, CH₂P⁺(C₄H₉)₃, Br⁻] | 112-3 |
| 12 | [structure with CF₃, Cl, O, CH₂P⁺(C₂H₅)₃, Br⁻] | 152-5 |

TABLE I-continued

| Compound Number | Structure | °C. Melt Pt. |
|---|---|---|
| 13 | CF$_3$—C$_6$H$_3$(Cl)—O—C$_6$H$_4$—CH$_2$P$^\oplus$(C$_6$H$_5$)$_3$  Br$^\ominus$ | 145-9 |
| 14 | C$_6$H$_4$(Cl)—O—C$_6$H$_4$—CH$_2$P$^\oplus$(C$_6$H$_5$)$_3$  Br$^\ominus$ | 118-22 |
| 15 | CF$_3$—C$_6$H$_4$—O—C$_6$H$_4$(CH$_2$P$^\oplus$(C$_6$H$_5$)$_3$)  Br$^\ominus$ | 91 |
| 16 | CF$_3$—C$_6$H$_3$(Cl)—O—C$_6$H$_3$(Cl)—CH$_2$P$^\oplus$(C$_4$H$_9$)$_3$  Br$^\ominus$ | 90 |
| 17 | CF$_3$—C$_6$H$_3$(Cl)—O—C$_6$H$_3$(Cl)—CH$_2$P$^\oplus$(C$_6$H$_5$)$_3$  Br$^\ominus$ | 100 |
| 18 | CF$_3$—C$_6$H$_3$(Cl)—O—C$_6$H$_3$(Cl)—CH$_2$P$^\oplus$(C$_2$H$_5$)$_3$  Br$^\ominus$ | 134-7 |
| 19 | C$_6$H$_5$—O—C$_6$H$_3$(Cl)—CH$_2$P$^\oplus$(C$_4$H$_9$)$_3$  Br$^\ominus$ | 84-8 |
| 20 | C$_6$H$_5$—O—C$_6$H$_3$(Cl)—CH$_2$P$^\oplus$(C$_6$H$_5$)$_3$  Br$^\ominus$ | 74-8 |
| 21 | C$_6$H$_5$—O—C$_6$H$_3$(Cl)—CH$_2$P$^\oplus$(C$_2$H$_5$)$_3$  Br$^\ominus$ | <25 |
| 22 | C$_6$H$_4$(Cl)—O—C$_6$H$_4$—CH$_2$P$^\oplus$(C$_4$H$_9$)$_3$  Cl$^\ominus$ | 159-60 |
| 23 | C$_6$H$_4$(Cl)—O—C$_6$H$_4$—C(=CH N(CH$_3$)$_2$)(P$^\oplus$(C$_6$H$_5$)$_3$)  Br$^\ominus$ | 50-8 |
| 24 | C$_6$H$_4$(Cl)—O—C$_6$H$_4$—CH(CHO)(P$^\oplus$(C$_6$H$_5$)$_3$)  Br$^\ominus$ | 184-8 |
| 25 | C$_6$H$_4$(Cl)—O—C$_6$H$_4$—C(=CHO$^\ominus$)(P$^\oplus$(C$_6$H$_5$)$_3$) | 75 |

A. PREPARATION OF COMPOUNDS 1-21

Of the above compounds, 1-21 were prepared by reacting the corresponding halogenated phenyl tolyl ether with N-bromo-succinimide in the liquid phase where carbon tetrachloride is employed as the solvent. The reaction was carried out in a glass reactor with constant mixing and irradiation with ultraviolet light in the presence of a catalytic amount of benzoyl peroxide. After conversion was effected, the corresponding halogenated phenoxybromotoluene was recovered by filtering to remove the insoluble by-product, i.e. succinimide, and then distilling off the carbon tetrachloride. The desired intermediate product, i.e. brominated ether derivative, was then purified by vacuum distillation. The recovered intermediate product was then dissolved in chloroform or xylene and reacted with phosphine in a sealed glass reactor with constant stirring to obtain the product corresponding to the Compound Number shown in the following Table II. Other conditions of the reactions are also reported in Table II.

TABLE II

PREPARATION OF COMPOUNDS 1 THROUGH 21 LISTED IN TABLE I

| Compound No. | gms of halogenated phenyl tolyl ether | reactn conds. temp.(°C./press. (psig)/time (hrs) | gms. N-bromo succinimide /mls. CCl$_4$ solvent | gm. halogenated phenoxy bromo-toluene deriv./ mls. solvent | gms of phosphine | reactn. conds. temp.(°C.)/press. (psig)/time (hrs) | Method of Recovery |
|---|---|---|---|---|---|---|---|
| 1. | 175g of Cl-C$_6$H$_3$(—O—C$_6$H$_4$—CH$_3$) | 77/atmospheric/24 | 185.1/500 | 29.7/50 xylene | 22.3g of P(C$_4$H$_9$)$_3$ | 25/atmospheric/2 | filtration followed by trituration with petroleum ether |
| 2. | 112g of Cl-C$_6$H$_4$—O—C$_6$H$_4$—CH$_3$ | 77/atmospheric/28 | 118/700 | 10/100 xylene | 7.4g of P(C$_4$H$_9$)$_3$ | 138/atmospheric/8.5 | filtration followed by trituration with xylene and then petroleum ether |
|  | 26g of |  |  |  | 4.2g of |  | evaporation to |

TABLE II-continued
PREPARATION OF COMPOUNDS 1 THROUGH 21 LISTED IN TABLE I

| Compound No. | gms of halogenated phenyl tolyl ether | reactn conds. temp.(°C./press. (psig)/time (hrs) | gms. N-bromo succini- mide /mls. CCl₄ solvent | gm. halogen ated phenoxy bromo- toluene deriv./ mls. solvent | gms of phosphine | reactn. conds. temp.(°C.)/press. (psig)/time (hrs) | Method of Recovery |
|---|---|---|---|---|---|---|---|
| 3. | 26g of F₃C—⟨⟩—O—⟨⟩—CH₃ | 77/atmospheric/18 | 19.8/100 | 7/25 CHCl₃ | P(C₄H₉)₃ | 25/atmospheric/16 | dryness followed by trituration with petroleum ether |
| 4. | 80g of F₃C—⟨⟩—O—⟨⟩—CH₃ | 77/atmospheric/18 | 19.8/100 | 5/25 CHCl₃ | 3g of P(C₂H₅)₃ | 25/atmospheric/20 | Same as #3 |
| 5. | 112g of Cl-⟨⟩—O—⟨⟩-CH₃ | 77/atmospheric/24 | 78.2/400 | 10/50 CHCl₃ | 4.4g of P(C₂H₅)₃ | 25/atmospheric/20 | Same as #3 |
| 6. | 175g of Cl-⟨⟩—O—⟨⟩—CH₃ | 77/atmospheric/28 | 118/700 | 5/25 CHCl₃ | 2.2g of P(C₂H₅)₃ | 25/atmospheric/20 | Same as #3 |
| 7. | 80g of Cl-⟨⟩—O—⟨⟩-CH₃ | 77/atmospheric/24 | 185.1/500 | 5/25 CHCl₃ | 2.2g of P(C₂H₅)₃ | 25/atmospheric/20 | Same as #3 |
| 8. | 112g of Cl-⟨⟩—O—⟨⟩-CH₃ | 77/atmopheric/24 | 78.2/400 | 10/50 CHCl₃ | 7.6g of P(C₄H₉)₃ | 25/atmospheric/20 | Same as #3 |
| 9. | 80g of Cl-⟨⟩—O—⟨⟩—CH₃ | 77/atmospheric/28 | 118/700 | 10/50 CHCl₃ | 10.3g of P(C₅H₆)₃ | 25/atmospheric/20 | Same as #3 |
| 10. | 51.2g of Cl-⟨⟩—O—⟨⟩-CH₃ | 77/atmospheric/24 | 78.2/400 | 10/50 CHCl₃ | 10.3g of P(C₆H₅)₃ | 25/atmospheric/20 | Same as #3 |
| 11. | 51.2g of F₃C—⟨⟩—O—⟨⟩-CH₃ | 77/atmospheric/22 | 41.6/200 | 10/50 CHCl₃ | 6.7g of P(C₄H₉)₃ | 25/atmospheric/20 | Same as #3 |
| 12. | 26g of F₃C—⟨⟩—O—⟨⟩-CH₃ | 77/atmospheric/22 | 41.6/200 | 10/50 CHCl₃ | 3.9g of P(C₂H₅)₃ | 25/atmospheric/20 | Same as #3 |
| 13. | 52g of F₃C—⟨⟩—O—⟨⟩—CH₃ | 77/atmospheric/18 | 19.8/100 | 10/50 CHCl₃ | 8.7g of P(C₆H₅)₃ | 25/atmospheric/20 | Same a #3 |
| | | | | | 10.3g of | | |

TABLE II-continued
PREPARATION OF COMPOUNDS 1 THROUGH 21 LISTED IN TABLE I

| Compound No. | gms of halogenated phenyl tolyl ether | reactn conds. temp.(°C./press. (psig)/time (hrs) | gms. N-bromo succinimide /mls. CCl4 solvent | gm. halogenated phenoxy bromotoluene deriv./ mls. solvent | gms of phosphine | reactn. conds. temp.(°C.)/press. (psig)/time (hrs) | Method of Recovery |
|---|---|---|---|---|---|---|---|
| 14. | 51.2g of 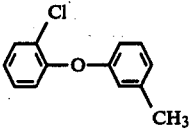 | 77/atmospheric/24 | 185.1/100 | 10/50 CHCl3 | P(C6H5)3 | 25/atmospheric/20 | Same as #3 |
| 15. | 64.8g of 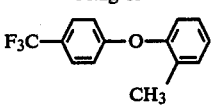 | 77/atmospheric/22 | 41.6/200 | 10/50 CHCl3 | 8.7g of P(C6H5)3 | 25/atmospheric/20 | Same as #3 |
| 16. | 64.8g of 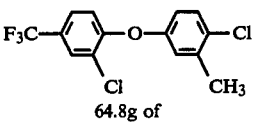 | 77/atmospheric/48 | 39.5/200 | 10/50 CHCl3 | 3.5g of P(C4H9)3 | 25/atmospheric/20 | Same as #3 |
| 17. | 66.8g of 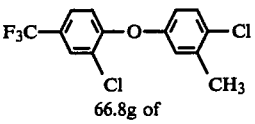 | 77/atmospheric/48 | 39.5/200 | 10/50 CHCl3 | 4.7g of P(C6H5)3 | 25/atmospheric/20 | Same as #3 |
| 18. | 45.5g of 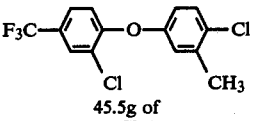 | 77/atmospheric/48 | 39.5/200 | 10/50 CHCl3 | 2.1g of P(C2H5)3 | 25/atmospheric/20 | Same as #3 |
| 19. | 45.5g of 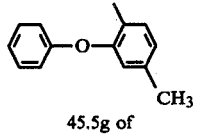 | 77/atmospheric/23 | 41/200 | 10/50 CHCl3 | 7.5g of P(C4H9)3 | 25/atmospheric/20 | Same as #3 |
| 20. | 45.5g of 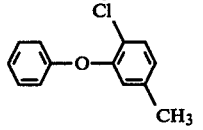 | 77/atmospheric/23 | 41/200 | 6.5/50 CHCl3 | 6.3g of P(C6H5)3 | 25/atmospheric/20 | Same as #3 |
| 21. | 45.5g of 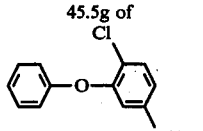 | 77/atmospheric/23 | 41/200 | 6.5/50 CHCl3 | 2.8g of P(C2H5)3 | 25/atmospheric/20 | Same as #3 |

5 5.5 3.5

B. PREPARATION OF COMPOUND 22

Compound 1 in the above Table I (5 g) was dissolved in 25 ml of chloroform and introduced into a reactor. To this solution was added a saturated solution of sodium chloride (100 ml) to form a 2 phase mixture and the resulting mixture was agitated at a temperature of 25° C. for 0.5 hour. The lower layer was drawn off, dried over anhydrous magnesium sulfate, filtered and evaporated to dryness to recover 4.2 g of 2-chlorophenoxy-3'-benzyltributylphosphonium chloride.

The corresponding chlorides of compounds 2 through 21 are prepared in a similar manner with concentrated aqueous solutions of potassium chloride or sodium chloride, e.g. saturated solutions by reacting at a temperature of from 25° C. to 100° C., e.g. 25° C. under atmospheric pressure and recovering the product as set forth above.

It is to be understood that the corresponding fluoride or iodide phosphonium salts of compounds 1 to 21 are similarly prepared by substituting saturated aqueous solutions of potassium fluoride or iodide or sodium fluoride or iodide in the above example.

C. PREPARATION OF COMPOUND 23

Compound 14 in Table I (5g) was dissolved in 30 ml of anhydrous propanol and introduced into a reactor. This solution was heated to 110° C. and 5.5g of dimethylaminodimethoxymethane was added. The reaction mixture was maintained at 110° C. and agitated for 32 hours at atmospheric pressure. The resulting reaction mixture was then evaporated to remove the solvent and triturated with 100 ml petroleum ether, after which it was dried to provide 3.5g of product.

It is to be understood that any of the corresponding fluoride, chloride or iodide phosphonium salts of compound 1 or any such salts of compounds 2 through 21 can be substituted in the above preparation C to provide the corresponding halogen-containing phenoxy styrylamino triphenyl phosphonium halide.

D. PREPARATION OF COMPOUND 24 OF TABLE I

The above Compound 23 (22 g) was introduced into a reactor wherein it was contacted with 165 ml of a 2 normal aqueous solution of hydrochloric acid at a temperature of 60° C. under atmospheric pressure for a period of 0.75 hour. The resulting product was then recovered by extraction with 200 ml of chloroform at room temperature and the chloroform vaporized by vacuum evaporation. The product is then triturated with petroleum ether to yield 10 g of product of over 95% purity.

It is to be understood that any of the corresponding fluoride, chloride or iodide phosphonium salts of the halogen-containing phenoxy styryl amino phosphonium bromides described in preparation C can be substituted in the above Preparation D to provide the corresponding aldehyde of the phosphonium salt.

E. PREPARATION OF COMPOUND 25 OF TABLE I

The above compound 24 (5 g) was dissolved in methanol (25 ml) and passed through a column of amberlite anion exchange resin (8.5 g of CG-4B, 200–400 mesh). After eluting the column with a further 20 ml of methanol the combined effluent was evaporated to dryness and the resulting oil triturated with cyclohexane (50 ml) and petroleum ether (50 ml) to yield 3 g of product.

It is to be understood that any of the corresponding fluoride, chloride or iodide phosphonium salts of the halogen-containing aldehyde described in preparation D can be substituted in the above preparation E to provide the corresponding dehydrohalogenated compound.

The compounds of the present invention can be applied alone as pesticides or can be employed in combination with an adjuvant in either liquid or solid form. The compositions containing the compounds of the present invention are prepared by admixing one or more of the present pesticides with the adjuvant including diluents, extenders, carriers or conditioning agents to provide compositions in the form of finely-divided particulate solids, granules, pellets, wetable powders, dusts, solutions and aqueous dispersions or emulsions. Illustrative of the granular solid carriers and extenders which may be employed include the talcs, clays, diatomaceous earth, silica, pumice, sulphur, walnut or coconut flour, wood dust, tobacco dust, charcoal and the like. Illustrative or the liquid carriers and extenders are water, propyleneglycol, N-methyl-pyrrolidone, benzene, xylene, cyclohexane and other liquid paraffins, acetone, methylethylketone, ethylketone, and other known extenders and carriers which may be employed singly or in combination. The formulations may also include a minor amount up to 8% of a surfactant which includes wetting agents, dispersing agents, suspending agents, and emulsifying agents. Typical of this group are the polyoxyethylene derivatives of fatty acid esters, imidazolines, etc. It is also to be understood that the formulations of the present invention may include other biocidally active components to achieve additional biocidal effects. Such combinations include mixtures of the present compounds with, e.g. Ethephon, Phosphon, Nitrofen, triacontanol, or other biocidally active compounds.

In selecting the appropriate rate of application of the present pesticides, it should be understood that the precise rates will be somewhat dependent upon the mode of application, such as soil incorporation, and pre-emergent or post-emergent plant treatment and foilar dusting or drench. Generally, for beneficial effects, the present compound or a mixture of the present compounds is applied in amounts of from about 0.05 to about 25 pounds per acre, or more. Preferably, applications of from about 0.1 to about 10 pounds per acre of active ingredient is employed. The concentration of the present compound either employed alone or in a formulation is between about 5 ppm and about 10,000 ppm, preferably between about 15 ppm and about 3,000 ppm, per plant, or an effective dosage for at least 80% plant response for the effect desired.

Having thus generally described the invention, reference is now had to the accompanying examples which serve to illustrate preferred and specific embodiments, but which are not to be construed as unduly limiting to the scope of the present invention as defined in the foregoing specification and in the appended claims. In the following examples, all amounts are by weight unless otherwise indicated. It is to be understood, that any of the foregoing compounds of this invention, as defined in Formula I or II or listed in Table II which are not exemplified in the following examples, can be substituted therein to provide the beneficial effects reported therein.

EXAMPLES 1–20

The activity of the compounds listed in Table I were tested as pesticides against two widely divergent species, namely the Mexican Bean Beetle and Southern Armyworm.

The pesticidal activity of the test compounds was examined at two dosage levels, i.e. 250 ppm and 33 ppm concentration of compound in solution. The solutions containing the test compound were prepared by introducing the compound as a solution of 90% water, 10% acetone containing 100 ppm Triton X-155 as a surfactant and then diluting the resulting solution with water to the required concentration, namely to 250 ppm and 33 ppm levels, as reported in Table III. Insecticides 9 and 13, which possessed an exceptionally high activity, were then additionally tested at 16 ppm and 8 ppm concentration levels as reported in Table IV.

For each compound tested, leaves of young bean plants from the same seed source and growing in sterilized soil under uniform conditions, were employed. Several leaves of these plants were removed by cutting the petioles, after which the severed leaves were dipped in the solution of test compound, (Groups A and A'). The petioles of the excised leaves were placed in a water reservoir to maintain leaf turgidity. After the solutions on the first group of leaves had dried, 5 larvae of the Mexican Bean Beetle were placed on each leaf. Observations on the mortality and the extent of inhibition of feeding of the beetles was made on an average of 2 to 3 days after infestation with the larvae and results reported in Table III. Both of these responses were rated from 0 (no effect on mortality or inhibition of feeding) to 100 (complete destruction of the larvae and consequent total inhibition of feeding). Similarly, after the solutions on the second group of excised plant leaves had dried, the leaves were infested with South Armyworm larvae (Groups B and B') by placing 5 larvae on each of the treated leaves. Again observations were averaged for 2-3 days after infestation and results reported in Table III. The excised leaves of groups A and B were dipped in 250 ppm test compound solution, whereas groups $A_1$ and $B_1$ were dipped in the 33 ppm test compound solution. The test compound numbers in the following tables correspond with the numbers assigned to specified compounds in Table I.

TABLE III

INSECTICIDAL ACTIVITY ON MEXICAN BEAN BEETLE AND SOUTHERN ARMYWORM

| | | Dosage Level - 250 ppm Test Compound | | | | Dosage Level - 33 ppm Test Compound | | | |
|---|---|---|---|---|---|---|---|---|---|
| | | Mexican Bean Beetle | | Southern Armyworm | | Mexican Bean Beetle | | Southern Armyworm | |
| Example No. | Test Coumpound No. | % Kill (A) | % Bean Inhibition (A) | % Kill (B) | % Feed Inhibition (B) | % Kill ($A_1$) | % Feed Inhibition ($A_1$) | % Kill ($B_1$) | % Feed Inhibition ($B_1$) |
| 1 | 1 | 80 | 90 | 0 | 60 | 15 | 40 | — | — |
| 2 | 2 | 100 | 100 | 0 | 60 | 20 | 40 | — | — |
| 3 | 3 | 100 | 90 | 0 | 30 | 55 | 70 | — | — |
| 4 | 4 | 100 | 90 | 0 | 20 | 5 | 35 | — | — |
| 5 | 5 | 100 | 90 | 0 | 10 | 80 | 5 | — | — |
| 6 | 8 | 100 | 90 | 0 | 50 | 55 | 70 | — | — |
| 7 | 9 | 100 | 80 | 0 | 40 | 100 | 90 | — | — |
| 8 | 11 | 100 | 80 | 0 | 30 | 0 | 20 | — | — |
| 9 | 13 | 100 | 100 | 60 | 70 | 100 | 90 | 0 | 45 |
| 10 | 22 | 100 | 90 | 0 | 30 | 0 | 20 | — | — |
| 11 | 14 | 100 | 100 | 0 | 40 | 50 | 65 | — | — |
| 12 | 15 | 100 | 60 | 0 | 10 | — | — | — | — |
| 13 | 16 | 100 | 80 | 0 | 20 | 0 | 20 | — | — |
| 14 | 17 | 80 | 70 | 0 | 10 | 35 | 45 | — | — |
| 15 | 18 | 100 | 80 | 0 | 10 | 0 | 25 | — | — |
| 16 | 20 | 70 | 80 | 0 | 10 | 20 | 30 | — | — |
| 17 | 23 | 90 | 60 | 0 | 40 | 15 | 25 | — | — |
| 18 | Phosphon | 100 | 60 | 0 | 40 | 0 | 20 | 0 | 30 |

The activities of compounds No. 9 and No. 13 were so superior that additional testing on Mexican Bean Beetle at 16 ppm and at 8 ppm concentrations was carried out in a manner similar to that set forth above. The results of these further tests are reported in following Table IV.

TABLE IV

| | | Insecticidal Activity | | | |
|---|---|---|---|---|---|
| | Test | 16 ppm Conc. | | 8 ppm Conc. | |
| Example No. | Compound No. | % Kill | % Feed Inhibition | % Kill | % Feed Inhibition |
| 19 | 9 | 90 | 70 | 80 | 60 |
| 20 | 13 | 95 | 70 | 40 | 35 |

What is claimed is:

1. A process for controlling insects on plants which comprises applying to said insects an insecticidally effective amount of a compound having the formula:

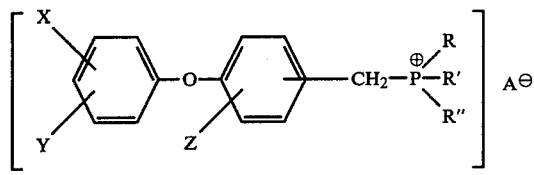

wherein $A^\ominus$ is a halogen anion; X, Y and X are each independently hydrogen, a halogen atom or a haloalkyl group of from 1 to 4 carbon atoms; R, R' and R" are each independently phenyl, halophenyl, haloalkylphenyl of from 7 to 12 carbon atoms or alkyl of from 1 to 6 carbon atoms, optionally substituted with halogen.

2. The process of claim 1 wherein R, R' and R" are phenyl radicals; X is hydrogen and Y is a substituent other than hydrogen.

3. The process of claim 1 wherein R, R' and R" are the same and are lower alkyl of $C_1$ to $C_6$ carbon atoms.

4. The process of claim 1 wherein said compound having the formula:

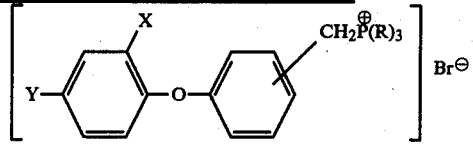

wherein X is hydrogen or chlorine; Y is hydrogen or trifluoromethyl, and wherein one of X and Y is other than hydrogen; and R is butyl or phenyl.

5. The process of claim 1 wherein said compound having the formula

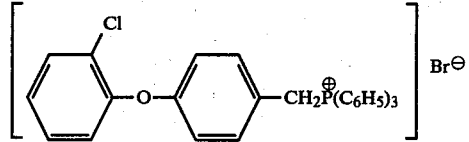

6. The process of claim 1 wherein said compound having the formula

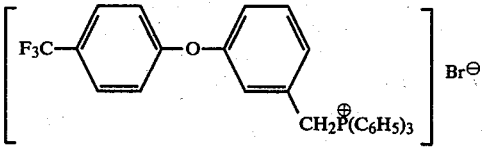

7. The process of claim 1 wherein said compound having the formula

8. The process of claim 1 wherein said compound having the formula

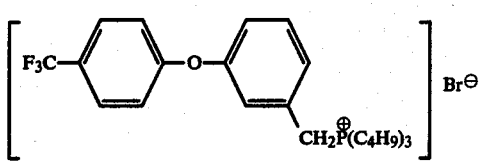

9. The process of claim 1 wherein said compound having the formula

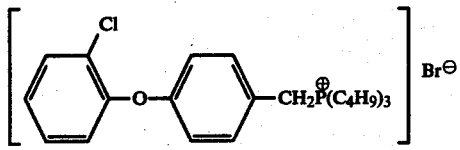

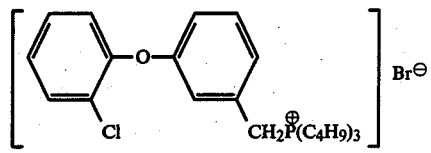

10. The process of claim 1 wherein the compound is mixed with an inert carrier in a concentration of between about 10 ppm and about 10,000 ppm to provide a formulation.

11. The process of claim 10 wherein the formulation is applied at a rate of between about 0.05 and about 25 lbs/acre.

12. The process of claim 1 wherein the compound is mixed with a carrier in a concentration of between about 15 ppm and about 3,000 ppm and is applied at a rate of between about 0.1 and about 10 lbs/acre.

13. The process of claim 10 which further contains a surfactant.

14. The process of claim 10 wherein said carrier is a particulate solid.

15. The process of claim 10 wherein said carrier is an aqueous solution.

* * * * *